(12) United States Patent
Correia De Costa et al.

(10) Patent No.: US 8,025,866 B2
(45) Date of Patent: Sep. 27, 2011

(54) DIAGNOSIS OF FASCIOLOSIS BY SKIN TEST (INTRADERMOREACTION) USING THE ANTIGEN FH8 (FASCIOLIN)

(75) Inventors: José Manuel Correia De Costa, Oliveira de Azeméis (PT); Maria Antónia Pereira De Conceicão, Coimbra (PT); Elisabete Marta Pereira Magalhães Da Silva, Vilar de Andorinho (PT); António Manuel Oliveira Castro, Vila Nova de Gaia (PT)

(73) Assignees: Instituto Nacional De Saude Dr., Lisboa (PT); Ricardo Jorge, I.P., Lisboa (PT)

(*) Notice: Subject to any disclaimer, the term of this patent is extended or adjusted under 35 U.S.C. 154(b) by 202 days.

(21) Appl. No.: 12/306,725

(22) PCT Filed: Jun. 27, 2007

(86) PCT No.: PCT/PT2007/000027
§ 371 (c)(1),
(2), (4) Date: Jan. 23, 2009

(87) PCT Pub. No.: WO2008/002166
PCT Pub. Date: Jan. 3, 2008

(65) Prior Publication Data
US 2010/0151482 A1 Jun. 17, 2010

(30) Foreign Application Priority Data
Jun. 27, 2006 (PT) .................................... 103510 K

(51) Int. Cl.
*A61K 49/00* (2006.01)
(52) U.S. Cl. ... 424/9.1; 424/810; 424/269.1; 424/191.1; 424/9.8; 424/9.81; 435/4

(58) Field of Classification Search ........................ None
See application file for complete search history.

(56) References Cited

OTHER PUBLICATIONS

Silva et al (J. Parasitol., 2004: 90 (4): 746-751).*
Robison et al (Phil. Trans. R. Soc. B Sep. 27, 2009 vol. 364 No. 1530 2763-2776).*

* cited by examiner

*Primary Examiner* — Jennifer Graser
(74) *Attorney, Agent, or Firm* — Kenealy Vaidya LLP

(57) ABSTRACT

Fasciolosis is an anthropozoonotic disease caused by the Trematoda *Fasciola hepatica*. This worm is a common parasite of ruminants namely sheep, goats and cattle. Adult worms are usually found in the bile ducts of the final host liver, causing significant economic losses in the animal husbandry industry. The diagnosis of *Fasciola hepatica* infection, in definitive hosts, is usually done by microscopic identification of parasite eggs in the stools, observation of adult worms in liver ducts, or by serology. However, no diagnostic tool as been described for utilization directly in the animals in the farm. The disclosed subject matter describes a cDNA clone codifying for a 69 amino acids polypeptide and 8 kDa molecular weight, and identified as Fh8 or "fasciolin" (Genbank number AF213970). Results show that the polypeptide FH8 act as an allergen. The disclosed subject matter is directed to the detection of *Fasciola hepatica*-infected definitive hosts using a skin application of "fasciolina" or related molecules obtained by mutation and chemical modification. The application system and the reading of the results can be specially executed for sheep and bovines, and it can be used in any kind of definitive host for this Trematoda. The test is easy to be used in field conditions and good results can be obtained faster.

4 Claims, 5 Drawing Sheets

Figure 1

```
  1  A A T T C G C G G C C G C T G T G C T C A T C
        M    P    S    V    Q    E    V    E    K    L    10
 24  ATG  CCT  AGT  GTT  GTT  GAG  GTT  GAA  AAA  CTC
        L    H    V    L    D    R    N    G    D    G    20
 54  CTT  CAT  GTT  CTC  GAT  CGC  AAC  GGT  GAC  GGG
        K    V    S    A    E    E    L    K    A    F    30
 84  AAG  GTT  TCT  GCC  GAG  GAG  TTG  AAA  GCC  TTC
        A    D    D    S    K    C    P    L    D    S    40
114  GCT  GAT  GAT  TCA  AAA  TGT  CCT  CTG  GAC  TCC
        N    K    I    K    A    F    I    K    E    H    50
144  AAT  AAG  ATC  AAG  GCT  TTC  ATT  AAG  GAA  CAC
        D    K    N    K    D    G    K    L    D    L    60
174  GAT  AAA  AAC  AAG  GAT  GGC  AAG  CTT  GAT  TTG
        K    E    L    V    S    I    L    S    S    70
204  AAA  GAA  CTC  GTT  TCG  ATT  TTG  TCA  TCA  TAG
234  A T T G T G T A T T A T G T G A A C C A T T A A A G A T A A C C
264  T T A T T C T G T A A A A A A A A A A A A A A A A A A A
294  A A A A A A A A A A A A A A A A A A G C G G C C G C G
```

Figure 2

```
Fh8      1M P S V Q E V E K L L H V L D R N G D G K V S A E E L K A F A
Fh8Ser   1 ----------------------------------------------------------------
Fh8Ala   1 ----------------------------------------------------------------
Fh8Tyr   1 ----------------------------------------------------------------

Fh8      32 D D S K C P L D S N K I K A F I K E H D K N K D G K L D L K E L
Fh8Ser   32 -------------S--------------------------------------------------
Fh8Ala   32 ----------A-----------------------------------------------------
Fh8Tyr   32 ---------- Y----------------------------------------------------

Fh8      64 V S I L S S
Fh8Ser   64 ------------------
Fh8Ala   64 ------------------
Fh8Tyr   64 ------------------
```

Figure 4
A
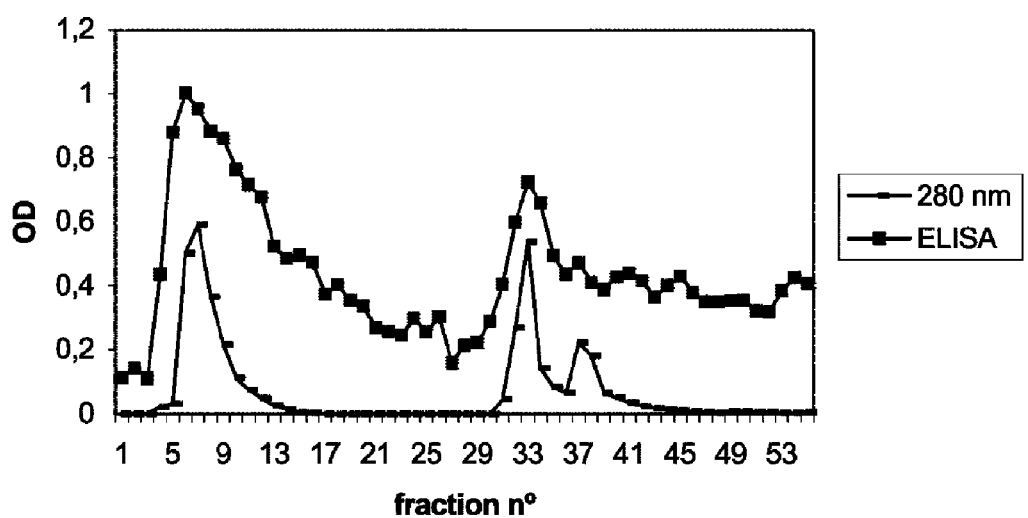
B
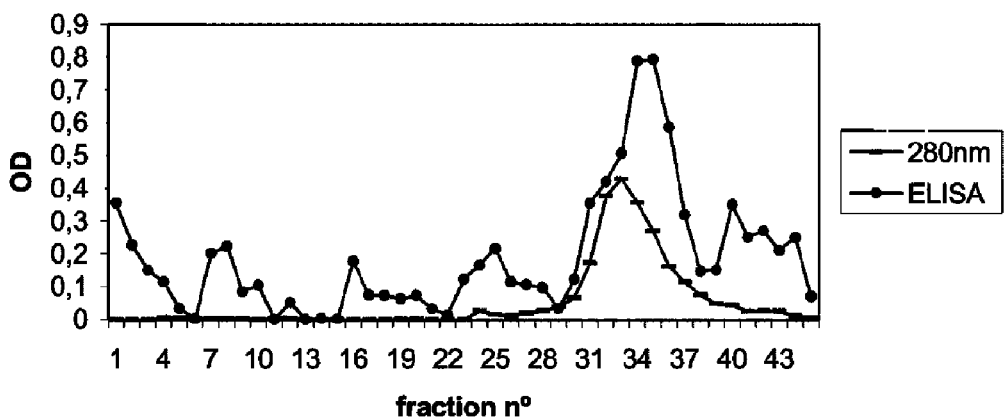

A

T=0  T= 1,5 horas

SEQUENCE LISTING

<160> NUMBER OF SEQ ID NOS: 1

<210> SEQ ID NO 1
<211> LENGTH: 69
<212> TYPE: PRT

-continued

```
<213> ORGANISM: Fasciola hepatica

<400> SEQUENCE: 1

Met Pro Ser Val Gln Glu Val Glu Lys Leu Leu His Val Leu Asp
1               5                   10                  15

Arg Asn Gly Asp Gly Lys Val Ser Ala Glu Glu Leu Lys Ala Phe
                20                  25                  30

Ala Asp Asp Ser Lys Cys Pro Leu Asp Ser Asn Lys Ile Lys Ala
                35                  40                  45

Phe Ile Lys Glu His Asp Lys Asn Lys Asp Gly Lys Leu Asp Leu
                50                  55                  60

Lys Glu Leu Val Ser Ile Leu Ser Ser
                65
```

DIAGNOSIS OF FASCIOLOSIS BY SKIN TEST (INTRADERMOREACTION) USING THE ANTIGEN FH8 (FASCIOLIN)

This application claims the priority benefit and is a National Stage application filed under 35 U.S.C. §371 of PCT/PT2007/000027 filed on 27 Jun. 2007, which claims priority under 35 U.S.C. §119 to Portuguese Patent Application No. 103510 filed on 27 Jun. 2006, which disclosure is hereby incorporated in its entirety by reference.

BRIEF DESCRIPTION OF FIGURES

FIG. 1: Characterization of the cDNA fragment containing the sequence corresponding to the polypeptide Fh8. Nucleotide sequence and amino acids sequence deduced for Fh8. The initial and terminal codons of the amino acids sequence are in black. The left numbers correspond to the nucleotide sequence and the right numbers correspond to amino acids residues.

FIG. 2: Fh8 protein sequence (fasciolin) and some site-directed mutant molecules (Fh8ser; Fh8ala; Fh8tyr).

FIG. 4: Fh8 Purification from adult worm *Fasciola hepatica* excreted/secreted antigens (ESA). A—Chromatography in Sephadex A25-DEAE column of ESA antigens precipitated by ammonium sulphate. The presence of the protein was quantified by 280 nm spectrophotometer and the Fh8 containing fractions were detected by ELISA test using a specific antisera (ELISA). B—Chromatography in a Sephacryl S200 HR of Fh8 containing fractions. Fractions were analyzed as described previously.

CONTEXTUALIZING THE SUBJECT

Figure 3:
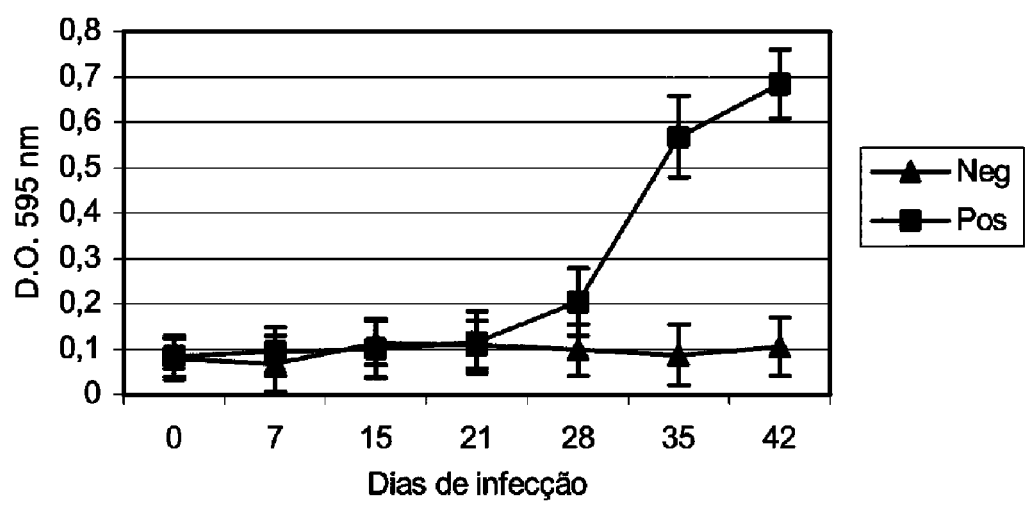
FIG. 3: ELISA test results using sera from Balb/c mice experimentally infected with 3 *Fasciola hepatica* metacercariae. Negative: O.D. values Media±standard deviation obtained with sera collected from 6 healthy and uninfected mice. Positive: O.D. values Media±standard deviation obtained with sera collected from 6 experimentally infected mice. O.D. Optical Density.

Fasciolosis is an anthropozoonotic disease caused by the trematode *Fasciola hepatica*. This worm is a common parasite of ruminants namely sheep, goats and cattle. Adult worms are usually found in the bile ducts of the host liver, causing significant economic losses in the animal husbandry industry (Boray, 1969).

Human cases of fasciolosis are uncommon but have been described worldwide. In Portugal human fasciolosis is a public health problem and several foci have been reported and studied. (Chen and Kenneth, 1990; Sampaio Silva et al., 1980)

The introductions of new methods have improved the diagnosis of human fasciolosis (Sampaio Silva et al., 1996; Silva et al. 2004) and the use of complementary parasitological and serological diagnostic tools allows the detection of most cases.

In Animal Production, diagnosis is most often based upon the detection of the worm and the liver lesions at the slaughterhouses. Diagnostic tools available for animal fasciolosis have improved significantly with the use of more specific antigens and sensitive methods. Nevertheless most available diagnostic tools showed low sensitivity or specificity (Boulard et al., 1985; Ibarra et al., 1998) hampering the implementation of a systematic diagnostic of the disease in farmed animals.

*F. hepatica* adult worm excreted/secreted antigens (ESA) have shown to be useful in the diagnosis of human fasciolosis, as their use has improved significantly the sensitivity and specificity of the tests (Sampaio Silva et al., 1996). Moreover, several authors have described the application of ESA in the serodiagnosis of cattle and sheep fasciolosis. Still no diagnostic tool for use in the field is currently available.

Due to their diagnostic and immunoprophylatic interest we have carried out the isolation of several cDNA clones coding for antigens homologues to ESA proteins (Castro, 2001; Eguino et al., 1999; Salazar-Caldéron et al., 2000; Silva et al. 2004). Several recombinant antigens have been produced and characterized. One of such recombinant antigens designated as rFh8, present in adult worm ESA and described and characterized elsewhere as a calcium-binding protein (Castro, 2001; Silva et al. 2004), is the subject of the current work.

Type 1 immediate hypersensitivity is characterized by the appearance of high levels of IgE antibodies after allergen presentation. Clinical aspects of fasciolosis including allergenic symptoms, high number of eosinophyls and high levels of specific IgE.

The utilization of skin tests for diagnosis of parasitic infections was described by many authors using worm crude extracts as antigen. Type I immediate hypersensitivity was used as a diagnostic tool for human fasciolosis. The method consists in a intra-dermal injection of a worm crude extract. Skin tests main advantages are the possibility of being used in the field, of simple execution and the obtaining of results is rapid.

Characterization of Fh8 (Fasciolin)

This antigen was previously purified and characterized by authors included in the inventors' list (Castro, 2001; Silva et al., 2004).

Fasciolin (Fh8) is a polypeptide with 69 amino acids and a molecular weight of 8 kDa (Genebank number AF213970). The main characteristic of Fh8 is the existence of 2 putative motives of calcium binding (EF-hand). Previous results showed that Fh8 is present in the excreted and secreted products of the adult worm. Several site-directed mutants were also prepared. These modified molecules are similar to Fh8 but present different stability and biological activity and may be an excellent alternative to Fh8.

For research purposes Fh8 coding sequence was subcloned in the *Escherichia coli* expression vector pQE (Qiagen). The production of the recombinant antigen, rFh8, expressing a N-terminal histidine tag was performed in *E. coli* M15 (pREP4) (Qiagen) according to supplier instructions (Castro, 2001; Silva et al. 2004). The production and isolation of the antigen is not relevant for the claims since other systems of expression and isolation of recombinant antigens as well as the native Fh8 isolated from ESA may be used. The described system of expression and isolation must be regarded as a vehicle used for research purposes to obtain large quantities of Fh8 used in experimental demonstrations, both in vivo and in vitro.

Fh8 has Diagnostic Interest in the Serology of Fasciolosis and Present Allergenic Characteristics.

Studies performed (Castro, 2001; Silva et al. 2004) with experimentally infected (with 30 or 100 *F. hepatica* metacercariae) rabbits showed the presence of specific immunoglobuline G (Ig G) against Fh8 from day 21 onwards. We have been to detect IgG against Fh8 in sera from sheep experimentally infected (from week 5 onwards) and cattle naturally infected.

Studies performed with sera from humans infected with fasciolosis (Silva et al. 2004) also indicated the presence of anti-Fh81 g G. These results demonstrate the diagnostic interest of Fh8 and proved that the worm produces the antigen during migration in final host. Several experiments to evaluate allergenic characteristics of Fh8 were also performed (Castro, 2001). In a first approach we detected the presence of specific Ig E against Fh8 in BALB/c mice experimentally infected with *F. hepatica*. Specific anti-Fh8 Ig E were detected from days 35 to 42 post-infection.

The immunization with 50 µg of Fh8 and incomplete Freund's adjuvant in BALB/c mice also induced the appearance of specific anti-Fh81 g E in the sera. These results allows to conclude that Fh8 has allergenic characteristics.

These results were the basic elements for the development of the invention with the purpose to detect ruminants infected with *F. hepatica* through the administration in vivo of Fh8 (fasciolin), or other antigen derived from Fh8 sequence, delivered in the skin. Another aspect of the invention concerns the formulation of the intradermal application and the read-out of the reactions occurring in sheep and cattle. Although formulations described concerns these two hosts the methodology may potentially be adapted to all the species that may be infected by *F. hepatica*.

Material and Method:

For research purposes Fh8 coding sequence was subcloned in the *Escherichia coli* expression vector pQE (Qiagen). The production of the recombinant antigen, rFh8, expressing a N-terminal histidine tag was performed in *E. coli* M15 (pREP4) (Qiagen) according to supplier instructions (Castro, 2001; Silva et al. 2004). The production and isolation of the antigen is not relevant for the claims since other systems of expression and isolation of recombinant antigens as well as the native Fh8 isolated from ESA may be used. The described system of expression and isolation must be regarded as a vehicle used for research purposes to obtain large quantities of Fh8 used in experimental demonstrations, both in vivo and in vitro.

Production and Isolation of rFh8:

For most experiments performed in vivo we used rFh8 produced in denaturating conditions. The rFh8 antigen represents more than 95% of the total protein content isolated (Castro, 2001). The production and isolation of rFh8 were performed according supplier instructions (Castro, 2001; Silva et al. 2004). Briefly, *Escherichia coli* M15 (pREP4) containing plasmid pQE31-Fh8 (harboring the Fh8 coding gene) were grown to exponential phase in Luria broth containing 100 µg/ml ampicilin and 50 µg/ml kanamicin. The cultures were incubated for 5 hours after adding 1 mM IPTG, and then collected by centrifugation and the cells were disrupted in 8 M urea pH 8.0. The recombinant antigen was purified by adsorption onto a Ni-NTA agarose (Qiagen) affinity column, according to the manufacturer protocols. The recombinant antigen was eluted using 8 M urea at pH 4.5.

Dialysis of rFh8 against 10 mM phosphate buffer, 2 mM NaCl pH 7.2 containing 2 mM EGTA, was performed overnight at 4° C.

Isolation of Fh8 from ESA:

Solid ammonium sulfate was added to 80% (w/v) saturation to 100 mg of ESP. After centrifugation, the protein pellet was resuspended in 5 ml of 10 mM phosphate, 0.1 M NaCl pH 7.2 and dialysed at 4° C. against the same buffer. The dialysed solution was centrifuged at 10000 rpm, 1 hour at 4° C. and applied to a DEAE-Sephadex A25 (Sigma) column (20 cm length, 1.5 cm internal diameter) pre-equilibrated in the same buffer. Elution was achieved with a linear gradient up to 0.5M of NaCl collecting 2.5 ml fractions. The presence of fasciolin was also investigated by ELISA using sera raised against recombinant antigen rFh8.

Samples containing high optical density (O.D.) values in ELISA were pooled and concentrated with Centricon YM3 (Amicon) to a final volume of 2 ml. The concentrate was dialysed overnight at 4° C. against PBS and loaded onto a pre-packed Sephacryl S200 HR column (Pharmacia) pre-equilibrated in PBS. Elution was performed collecting 2.5 ml samples. The presence of fasciolin was also investigated by ELISA using sera raised against recombinant antigen rFh8.

Preparation of the Antigen for Use in Skin Tests:

The antigen was dialysed overnight against phosphate buffer 10 mM, pH 7.2 and submitted to removal of pirogens using a agarose-mitomixin C (Pierce) column according to instructions from the supplier. The obtained antigen solution was sterilized by filtration by a 0.22 µm membrane and stored at −20° C. Previously to it's use in skin tests the antigen was diluted to the appropriate concentration in sterile and apirogénic 10 mM phosphate buffer pH 7.2.

Experimental and Natural Infections:

Experimental infections were performed in Black Merino Strain (groups of 4) with 8 months (first experimental infection) or 4 months (second experimental infections) kept in the installations of Escola Superior Agrária de Coimbra in agreement with recommendations from the Direcção Geral de Veterinária (institution responsible for the application of animal well-fare laws). Sheep were infected with 200 *F. hepatica* metacercareae and the presence of the parasite was evaluated using coprologic and serologic methods. Sheep naturally infected with *F. hepatica* were sheep from ESAC introduced in flocks from endemic areas. Cattle naturally infected were detected in the region of Vagos (Portugal) by the presence of *F. hepatica* eggs in the stools. Assays performed in naturally infected sheep and cattle were performed with the agreement of the owners in the presence of veterinarians from local OPP (Organização de Produtores Pecuários).

Evaluation of the Use of Fh8 in the Detection of Infections with *F. hepatica* by Skin Test:

The goals of experiments with experimentally infected sheep were to evaluate and characterise the hipersensibility reaction occurring where Fh8 was delivered, the optimal formulation of the application and the optimal skin location to apply the antigen.

Experiments performed in naturally infected cattle were performed in the skin of the neck and were used to characterise the formulation to obtain a significant reaction.

Used formulation consisted in 200 µl of a sterile and apirogénic 10 mM phosphate solution, 2 mM CaCl2 containing the adequate concentration of Fh8. Application were intradermic using syringe for intradermoreaction.

Results

Figure 5:
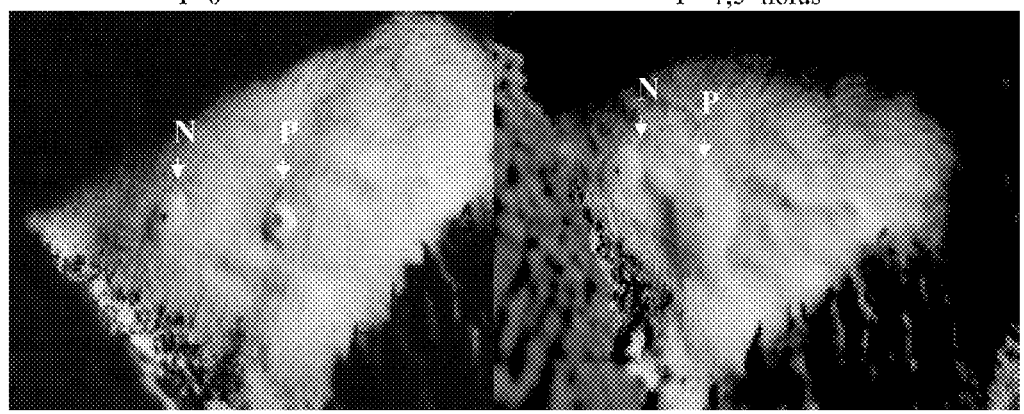
FIG. 5: Skin reactions (papules) observed in sheep 2 (A) and 4 (B) (Table 1). We have proceed to the skin (intradermal) injection of 200 µl of buffer (N) and 200 µl buffer plus 50 µg of Fh8 (P) in the internal area of the legs of 2 experimentally infected sheep. The photos show the evolution of the papule at (T=0), immediately after injection, and (T=1,5), one hour and a half after the injection, and also the means used to measure the papule.

For the evaluation of the reaction of delayed hypersensitivity and its evolution we proceed to the intradermal injection of 200 µl of phosphate buffer containing 50 µg of Fh8 and 200 µl of phosphate buffer in two areas of the internal thigh of the animal (FIG. 5). It was proceeded the analysis of the reaction of immediate hypersensitivity and was observed, in the same places of the application of the Fh8, a similar evolution to the one described in table 1.

TABLE 1

Evaluation of the immediate hypersensitivity reaction in sheep experimentaly infected with 200 metacercarieae of *F. hepatica*.

| Sheep | Size of the swell (cm) | | | | | | Skin thickening (mm) | |
|---|---|---|---|---|---|---|---|---|
| | 0 min. | 10 min. | 20 min. | 45 min. | 1 hora | 2 horas | NEG | POS |
| 1 | 0.9 | 0 | 0 | 2.3 × 1.0 | 2.0 × 1.3 | 3.0 × 2.0 | 1 | 5 |
| 2 | 0.9 | 0 | 0 | 0 | 1.5 × 1.3 | 2.5 × 1.5 | 1 | 3 |
| 3 | 0.9 | 0 | 0 | 1.2 × 1.0 | 1.0 × 1.0 | 2.0 × 1.0 | 1 | 4 |
| 4 | 0.9 | 0 | 0 | 3.0 × 3.0 | 2.0 × 1.5 | 2.0 × 1.3 | 1 | 3 |

Swelling - size of the swell observed in the place of Fh8 application throughout the time.
Thickening - values of the skin thickening in the place of Fh8 application (POS) and buffer without antigen (NEG) 2 hours after intradermal injection.
min. - minutes.

After application it is developed a small swell in the place of the application, as much in the place of application of the Fh8 as of the buffer. This swell diminishes quickly and disappears about 10 minutes after application. In the places of application of the buffer, in both the infect and non-infected sheep, and also in the place of Fh8 application in the non-infected sheep, it is not observed the appearance of immediate hypersensitivity reaction, not having been observed any swelling. In the places of the application of Fh8, in the experimentally infected sheep, it is observed in the majority of the animals, to the end of 30-45 min., of an area of redness around the application place. At this time it starts to be visible one swell in the place of application of the Fh8. The area of swell is grows, reaching its maximum size about 1.5 to 2 hours after-injection. From 1 hour it is observed a significant increase of the thickness of the skin in the application place, that reaches the maximum about 1.5 to 2 hours after-injection (Table 1). After 2.5 hours starts to be observed a reduction of the consistency and dimensions of the swell as well as the thickening of the skin that disappears about 4 to 5 hours after-application. It was not observed any reaction or significant alteration of the skin in the place of the application 24 and 48 hours after-application.

The obtained results demonstrate that the Fh8 antigen is capable to induce, in the animals infected by *F. hepatica*, an immediate hypersensitivity reaction that could be used for identification of animals infected with the parasite. The reaction is detected visually, for the significant appearance of a swell in the place of the application between 1 and 2 hours after-application, or by thickening of the skin in the place of the application that should be superior in 1 mm in relation to the thickness before the application of the antigen. These results are related to the sheep as the definitive host.

It was proceeded the analysis of the potential places of application of the polipeptide in the sheep model making simultaneous applications of the Fh8 in the internal thigh, in the armpit and in the external part of the ear. The applications performed were made with 40 µg of the polipeptide and it was observed similar reactions to the ones previously described in all the places of application.

TABLE 2

Immediate hipersensitivity reaction in the experimentally infected sheep with 200 metacercarieae of *F. hepatica*. Four non-infected sheep (1, 2, 3 e 4) and 4 infected sheep (5, 6, 7 e 8) were subjected to intradermal injections of 200 µl of buffer, 200 µl of buffer containing 10, 20 or 40 µg de Fh8 into different places of the external part of the ear. The thickening of the skin was evaluated in each application place at the end of 1.5 hours.

| Sample | Non-infected sheep - thickening (mm) | | | | Sheep infected with *F. hepatica* - thickening (mm) | | | |
|---|---|---|---|---|---|---|---|---|
| | 1 | 2 | 3 | 4 | 5 | 6 | 7 | 8 |
| Buffer | 1.5 | 1.5 | 1.5 | 1.5 | 2.0 | 1.5 | 2.0 | 1.5 |
| 10 µg of Fh8 | 1.5 | 1.5 | 1.5 | 1.5 | 4.0 | 1.5 | 2.5 | 3.0 |
| 20 µg of Fh8 | 1.5 | 1.5 | 1.5 | 1.5 | 4.0 | 2.0 | 3.0 | 3.5 |
| 40 µg of Fh8 | 1.5 | 1.5 | 1.5 | 1.5 | 3.5 | 3.0 | 5.0 | 3.5 |

Some experiences were performed in order to evaluate the dose of the antigen to apply for observing the reaction and it was verified the presence of reaction in the applications containing 10 µg of Fh8 (Table 2). These determinations and the posterior applications had been performed in the external part of the ear, which presents advantages in terms of easiness in the cutaneous application, and the reading of the reaction. This is due to taking off of the skin of the cartilage in the swelling process and reading of the thickening of the skin.

In the experiments performed in naturally infected sheep with fasciolose we observe similar reactions to the ones previously described.

The assays performed in bovines had been all carried through with naturally infected animals with *F. hepatica*. 3 concentrations of the Fh8 had been tested (50 µg, 25 µg and 5 µg in each application) having been observed an evolution of the immediate hypersensitivity reaction with some differences in comparison with sheep. In this case, the reaction is processed in a faster way been able the observation of the thickening of the skin at the end of 15-20 minutes. In the case of the negatives, the liquid is absorbed after 2-3 minutes not been observed the presence of any reaction or alteration in the skin.

In the positive reactions it can be observed, depending on the amount of applied antigen and the animal, the appearance of an visible swell starting at 15-20 minutes that evolve increasing of size until about the 1.5 hours diminishing later slowly. It is also verified in some cases a ganglia reaction with an increase of the pre-escapular ganglion. The reaction disappears at the end of 5-6 hours not been observed any nodule in the application places or any reaction to the end of 24 and 48 hours. In the case of the bovines the presence of the worm is evaluated to the 15-20 end minutes by the thickening of the skin equal or over 1 mm relatively to the reading performed before the application. It was observed reactions for all the used antigen concentrations.

The studies performed with Fh8 mutants, namely the ones described in FIG. 2, had shown that these antigens have similar characteristics to the Fh8, being able to be potentially used in substitution of this polipeptide. The mutants could present advantages to the level of the production and isolation, to the level of the polipeptide conservation and to the level of the polipeptide activity.

CONCLUSION

The Fh8 polipeptide revealed ability to originate the appearance of an immediate hypersensitivity reaction in definitive hosts infected with *F. hepatica* worm. It was experimentally demonstrated that this reaction can be used to detect the infection caused by the worm in vivo being an fast and easy method to diagnosis the infection in the field by the veterinarian itself. The commercially available methods present some disadvantages, namely to be expensive and to imply the harvest of blood or excrements for analysis in laboratory. The developed methodology will allow the evaluation of the illness in the animal or flock and respective treatment for the veterinarian reducing greatly the time spent for the diagnosis and being able to be an instrument with great interest in the combat to the illness.

The application analyzed until the moment consisted of an intradermoreaction, however, it could be used other forms of cutaneous applications according to the host to be analyzed, namely at the human level.

The evaluations performed had demonstrated that the reaction does not originate any secondary effect or the posterior development of nodules or cutaneous alterations.

The formularization of the cutaneous application and reaction reading will have to be adapted to the species in evaluation having been presented the applicable conditions to sheep and bovines.

BIBLIOGRAPHY

Boulard, C., M. Bouvry, and G. Argeinte. 1985. Comparison of the detection of foci of fasciolosis by the ELISA test on lactoserum and serum and coproscopy. Ann. Res. Vet., 16 (4): 363-368.

Castro, A. M. 2001. Obtençáo e caracterizaçáo de proteínas recombinantes homólogas de antigénios excretados/secretados pelo verme adulto de *Fasciola hepatica*. Ph.D. thesis. Universidade do Porto.

Chen M G and Kenneth E M. Progress in assessment of morbidity due to *Fasciola hepatica* infection: a review of recent literature. Trop Dis Bull 1990; 8: 1-38.

Eguino A R, Machín A, Casais R, Castro A, Boga J, Martín-Alonso J, Parra F. Cloning and expression in *Escherichia coli* of a gene encoding a calcium-binding protein. Mol Biochem Parasitol 1999; 101: 13-21.

Ibarra, F., N. Montenegro, Y. Vera, C. Boulard, H. Quiroz, J. Flores, and P. Ochoa. 1998. Comparison of three ELISA tests for epidemiology of bovine fasciolosis. Vet. Parasitol., 77: 229-236.

Salazar-caldéron M, Martin-Alonso J M, Ruiz de Eguino A D, Casais R., Marin M S and Parra F. *Fasciola hepatica*: heterologous expression and functional characterization of a thioredoxin peroxidase. Exp Parasitol 2000; 95: 63-70.

Sampaio Silva M L, Capron A and Capron M. Human fascioliasis in Portugal. Arquivos do Instituto Nacional de Saúde 1980; 4: 101-109.

Sampaio Silva M L, Correia da Costa J M, Viana da Costa A M, Pires M A, Lopes S A and Monjour L. Antigenic components of excretory-secretory products of adult *Fasciola hepatica* recognized in human infections. Am J Trop Med Hyg 1996; 54 (2): 146-8.

Silva E., Castro A., Lopes A., Rodrigues A., Dias C., Conceição A., Alonso J., Correia da Costa J. M., Bastos M., Parra F., Moradas-Ferreira P. and Silva M. A recombinant antigen recognized by *Fasciola hepatica*-infected hosts. J. Parasitol., 2004: 90 (4): 746-751.

Sequence ID 1

Size: 69

Type: proteína

Organism: *Fasciola hepatica*

```
                                                     Sequence: 1
    Met Pro Ser Val Gln Glu Val Glu Lys Leu Leu His
                                             10

Val Leu Asp Arg Asn Gly Asp Gly Lys Val Ser Ala
                                 20

Glu Glu Leu Lys Ala Phe Ala Asp Asp Ser Lys Cys
                             30

Pro Leu Asp Ser Asn Lys Ile Lys Ala Phe Ile Lys
                         40

Glu His Asp Lys Asn Lys Asp Gly Lys Leu Asp Leu
            50                                   60

Lys Glu Leu Val Ser Ile Leu Ser Ser
                                     69
```

It will be apparent to those skilled in the art that various modifications and variations can be made in the presently disclosed subject matter without departing from the spirit or scope of the invention. Thus, it is intended that the presently disclosed subject matter cover the modifications and variations of the presently disclosed subject matter provided they come within the scope of the appended claims and their equivalents. All related art references described above and described in the Bibliography section of the present specification are hereby incorporated in their entirety by reference.

What we claim is:

1. A method of diagnosing the presence of a fascilosis infection in a host, said method comprising:
    delivering a polypeptide comprising an isolated Fh8 antigen having the amino acid sequence of SEQ ID NO: 1 into the skin of the host; and
    assaying for the induction of an immediate hypersensitivity reaction characteristic of *Fasciola hepatica* infection.

2. The method of claim 1 wherein the Fh8 antigen comprises the amino acid sequence of SEQ ID NO: 1 wherein the cysteine residue at amino acid position 36 has been modified to an amino acid residue selected from the group consisting of serine, alanine, and valine.

3. The method of claim 1 wherein the polypeptide is delivered to the host by intradermal injection into the skin.

4. The method of claim 1 wherein the host to be diagnosed is selected from the group consisting of cattle, sheep and humans.

* * * * *